US012735995B2

(12) United States Patent
Cukurel

(10) Patent No.: US 12,735,995 B2
(45) Date of Patent: Sep. 15, 2026

(54) ADDITIVELY MANUFACTURED GAS TURBINE ENGINE AND VENTILATOR

(71) Applicant: TECHNION RESEARCH & DEVELOPMENT FOUNDATION LIMITED, Haifa (IL)

(72) Inventor: Beni Cukurel, Kibbutz Nahsholim (IL)

(73) Assignee: TECHNION RESEARCH AND DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 17/915,542

(22) PCT Filed: Apr. 3, 2021

(86) PCT No.: PCT/IB2021/052796
§ 371 (c)(1),
(2) Date: Sep. 29, 2022

(87) PCT Pub. No.: WO2021/199007
PCT Pub. Date: Oct. 7, 2021

(65) Prior Publication Data

US 2023/0143187 A1 May 11, 2023

Related U.S. Application Data

(60) Provisional application No. 63/112,187, filed on Nov. 11, 2020, provisional application No. 63/004,543, filed on Apr. 3, 2020.

(51) Int. Cl.
*F01D 25/16* (2006.01)
*A61M 16/00* (2006.01)
(Continued)

(52) U.S. Cl.
CPC ......... *F01D 25/16* (2013.01); *A61M 16/0066* (2013.01); *A61M 16/1005* (2014.02);
(Continued)

(58) Field of Classification Search
CPC ........ F01D 25/16; F01D 25/162; F01D 25/18; F01D 25/24; F02C 1/02; F02C 3/06;
(Continued)

(56) References Cited

U.S. PATENT DOCUMENTS 3,126,703 A * 3/1964 Oprecht .................... F23R 3/38 415/176
4,195,475 A * 4/1980 Verdouw ................. F23R 3/002 60/754

(Continued)

FOREIGN PATENT DOCUMENTS

CN 108590859 A 9/2018
KR 101937770 B1 1/2019

OTHER PUBLICATIONS

Extended European Search Report in EP application No. 21780168.7, dated Mar. 19, 2024, 7 pages.

(Continued)

*Primary Examiner* — Steven M Sutherland
(74) *Attorney, Agent, or Firm* — AlphaPatent Associates Ltd.; Daniel J. Swirsky

(57) ABSTRACT

A gas turbine engine with a rotor comprising a turbine and compressor, mounted in a housing surrounding the rotor. The rotor rotates on one or more hydro bearings, the profiles of the outer surface of the rotor and the inner surface of the housing generating the hydro bearing(s). A combustion chamber is formed within the housing, and the combustion products of the fuel/air mixture are directed from the combustion chamber to the turbine. The housing and rotor are formed by an additive manufacturing process in a single procedure, with the rotor enclosed within the housing, and unsupported by any mechanical connections. A gas turbine respiratory ventilator system is described using a compressed oxygen flow to power the turbine which rotates the centrifugal blower for generating the air flow for respiration (Continued)

of the patient. The oxygen exhausted from the turbine can then be used to supplement the air flow.

10 Claims, 8 Drawing Sheets

(51) Int. Cl.
*A61M 16/10* (2006.01)
*F02C 1/02* (2006.01)
*F02C 3/06* (2006.01)

(52) U.S. Cl.
CPC .................. *F02C 1/02* (2013.01); *F02C 3/06* (2013.01); *F05D 2220/30* (2013.01); *F05D 2220/32* (2013.01); *F05D 2230/31* (2013.01); *F05D 2240/53* (2013.01)

(58) Field of Classification Search
CPC .... F02C 7/06; F05D 2220/30; F05D 2220/32; F05D 2230/31; F05D 2240/53
See application file for complete search history.

(56) References Cited

U.S. PATENT DOCUMENTS

| | | | | |
|---|---|---|---|---|
| 5,403,165 | A * | 4/1995 | Lehe | F04D 13/04 417/406 |
| 5,454,222 | A | 10/1995 | Dev | |
| 5,932,940 | A | 8/1999 | Epstein et al. | |
| 6,866,478 | B2 | 3/2005 | Fabian et al. | |
| 10,465,603 | B1 | 11/2019 | Sachdev et al. | |
| 2003/0215323 | A1 | 11/2003 | Prinz et al. | |
| 2004/0057826 | A1* | 3/2004 | Haje | F01D 25/16 415/170.1 |
| 2006/0090447 | A1* | 5/2006 | Jeske | F02C 3/305 60/39.53 |
| 2013/0039739 | A1* | 2/2013 | Milne | F02C 7/28 415/13 |
| 2013/0098061 | A1 | 4/2013 | Matwey et al. | |
| 2013/0251501 | A1* | 9/2013 | Araki | F01D 25/24 415/182.1 |
| 2014/0050559 | A1* | 2/2014 | James | F01D 11/06 415/170.1 |
| 2014/0125066 | A1 | 5/2014 | Baumgart | |
| 2014/0169971 | A1 | 6/2014 | Vedula et al. | |
| 2015/0275691 | A1 | 10/2015 | Kerogh et al. | |
| 2016/0102608 | A1* | 4/2016 | Lynn | F01D 9/02 60/722 |
| 2020/0040739 | A1 | 2/2020 | Notarnicola et al. | |
| 2020/0400314 | A1 | 12/2020 | Binek et al. | |

OTHER PUBLICATIONS

Non-Final Rejection in U.S. Appl. No. 17/792,151; dated Apr. 16, 2025, 17 pages.

Epstein, A. H. "Millimeter-Scale, micro-electro-mechanical systems gas turbine engines", Journal of engineering for gas turbines and power vol. 126 No. 2 (2004): pp. 205-226, The American Society of Mechanical Engineers, NY. NY, USA.

Tanaka, S. Isomura, K. Togo, S. I., Esashi, M. "Turbo test rig with hydoinertia air bearings for a palmtop gas turbine." Journal of Micromechanics and Microengineering vol. 14 No. 11 (2004): pp. 1449-1454, IOP Publishing, Bristok, GB.

Seo, Jeongmin, et al. "Development and experimental investigation of a 500-W class ultra-micro gas turbine power generator." Energy 124 (2017): 9-18, Elsevier, Amsterdam, NL.

Peirs, J., Waumans, T., Vleugels, P., Al-Bender, F., Stevens, T., Verstraete, T., Vanden Braembussche, R. "Micropower generation with microgasturbines: a challenge." Proceedings of the Institution of Mechanical Engineers, Part C: Journal of Mechanical Engineering Science vol. 221 No. 4 (2007): pp. 489-500, Institution of Mechanical Engineers, London, GB.

Kang, S., Johnston, J. P., Arima T., Matsunaga, M., Tsuru, H., Printz, F. B. "Microscale radial-flow compressor impeller made of silicon nitride: manufacturing and performance." Journal of engineering for gas turbines and power vol. 126 No. 2 (2004): pp. 358-365, The American Society of Mechanical Engineers, NY. NY, USA.

Dessornes, O,. Landais, S., Valle, R., Fourmaux, A., Burguburu, S., Zwyssig, C., Kozanecki, Z. "Advances in the development of a Microturbine Engine." Journal of engineering for gas turbines and power vol. 136 No. 7 (2014): p. 71201, The American Society of Mechanical Engineers, NY. NY, USA.

* cited by examiner

ADDITIVELY MANUFACTURED GAS TURBINE ENGINE AND VENTILATOR

FIELD

The present invention relates to the field of gas turbine engines, especially for use in rapid and inexpensive manufacture of engines for propulsion, power generation, or for respiratory ventilation applications.

BACKGROUND

The challenge to rapidly manufacture large quantities of mechanical ventilators is an issue of global significance due to the ongoing COVID-19 pandemic. Modern ventilator units provide mechanical ventilation by moving breathable air into and out of the lungs. They are typically expensive machines, with significant production costs. The required air flow is typically generated by a controlled turbo-pump or blower, driven by an electric motor. Ventilators are capable of providing a necessary volume of air, which is usually supplemented with additional oxygen, to patients in respiratory distress and unable to execute sufficiently effective spontaneous breathing, according to the desired respiratory rate of the individual being ventilated. Current ventilators generally use a variable speed blower, with features that allow control of oxygen saturation and ventilating modes close to the patient's natural breathing pattern. The ventilator is typically driven by a brushless electric motor, though other forms of drive have also been used.

However, when a major pandemic occurs, such as the present SARS-CoV-2 outbreak, the number of ventilators required may outstrip the available number in any medical environment, and in many global settings, the need for the provision of large numbers of ventilators over a short range of time may be critical, resulting in short supply of this critical equipment. Given the tendency of viruses such as SARS-CoV-2 to mutate rapidly during their global dispersion, the uncertainty of our ability to control the diseases caused by these viruses, and the unknown possibility of future pandemics causing acute and widespread respiratory distress requiring ventilator support, the ability to supply inexpensive ventilators, and to do so rapidly, could save many lives. There therefore exists a need for inexpensive, efficient, rapidly producible, and portable mechanical ventilators, with precisely replicable parts which overcome at least some of the disadvantages of prior art systems and methods.

Unmanned aerial vehicles (UAV) capture an ever-increasing part of our daily operations. This is especially true for small scale UAVs, which are commonly powered by micro-gas turbines. These micro jet engines have thrust rating below 1 kN and have disproportionate cost for both disposable and re-usable platforms. Moreover, in multi-mission platforms, significant efforts are invested towards prolonging the service life of these small yet expensive engines, and maintenance becomes an important subject, which involves long chain of suppliers and overall work expenditures that have the potential to even exceed the base price of the engine. Instead of relying on these paradigms, extremely cheap limited-life micro-jet engines have the potential to eliminate supply chains, warehousing of replacement parts, maintenance procedures, and all expenses associated with it. However, despite the relatively simple design of a conventional micro-turbojet engine, its manufacturing involves long and costly processes due to presence of numerous parts, different manufacturing methods, logistics of various subcontractors and collaboration of different departments that assemble and qualify the product. In view of the high capital cost, and the high maintenance costs for such micro-gas turbine engines, it would be advantageous to device a method of manufacturing such engines at a substantially reduced cost to those currently available.

The disclosures of each of the publications mentioned in this section and in other sections of the specification, are hereby incorporated by reference, each in its entirety.

SUMMARY

The present disclosure describes new exemplary systems for rapid and low-cost production of turbine engines, such as for use for propulsion, or in ventilation systems, by means of additive manufacturing methods.

According to a first implementation described in this disclosure, there is provided a gas turbine engine whose manufacturing process involves three-dimensional additive manufacturing to form both the housing and the turbine-compressor impeller or unit in a single process, with the internal impeller formed "trapped" inside the outer housing, and with hydro bearing surfaces separating the two components.

Additive manufacturing technologies have seen significant advances in recent years. These technologies have begun to supplant classical subtractive based manufacturing methodologies and are gaining an increasing share of the manufacturing market. This is due to new, innovative possibilities to manufacture complex geometries, and the relatively low cost in comparison to more conventional manufacturing techniques. These prospects have increased interest for such techniques in different industries such as aerospace, automotive and medicine. There are various 3D printing technologies on the market which differ from each other by means of the original material supply and the technique used to fuse layers into a complete solid model. This manufacturing process also provides a commercial advantage, in that it enables the manufacture of completely assembled products, such as turbine engines and the ventilator blower units described below, with minimum lead time, and without the need for assembly steps and for stocking parts of the device.

Such gas turbine engines may be used for providing the thrust in other applications, such as lightweight, unmanned aircraft or drones powered by fuel or another energy source.

In one exemplary implementation of the disclosed devices, a three-dimensional printed motor is used with a fuel source as a low cost gas turbine engine, such as is suitable for powering unmanned aerial vehicles (UAV). Small scale UAVs, are commonly powered by assembled micro-gas turbine engines, with thrust ratings below 1 kN. Such engines often have a disproportionately high cost that varies from 30,000 to 150,000 USD, and sometimes even more. For both single-use and reusable platforms, conventional engine is manufactured by assembling pre-produced component parts, inflates the system cost dramatically. Moreover, in multi-mission platforms, significant efforts may be invested to prolong the service life of these small yet expensive engines. Maintenance, which involves a long chain of suppliers and overall work expenditure, thus becomes an important component of cost, and can even exceed the base price of the engine.

Conventional micro-turbojet engine manufacturing involves long and costly processes due to the numerous parts, different manufacturing and assembly methods, logistics of various subcontractors and collaboration of different departments that assemble and qualify the product. The present disclosure enables the production of lower cost micro-jet engines having the potential to eliminate supply chains, warehousing of replacement parts, maintenance procedures, and other expenses associated therewith. Instead of relying on this conventional process, the present disclosure provides a novel gas turbine engine that can be additively manufactured in its final topology through a single uninterrupted printing process that encompasses both the rotating and stationary components. Requiring only a three-dimensional printer, the cost of the engine will be reduced to little more than the capital equipment depreciation, the raw material, and minimal operator supervision of the process, with an expected cost reduced to a small fraction of the current gas turbine engine cost.

Considering the print volume of the currently available 3-D printers, the engine may have a diameter of up to 30 cm, thrust rating of 650 N and air mass flow rate of about 1.4 kg/s, though it is to be understood that this characterizes the presently available engine size, and increase in size is expected as 3-D printing technology includes larger scale volumes. The proposed manufacturing method also enables a reduction in the number of components. Thus, the engine includes only two major parts—a static casing with embedded combustion chamber and a rotating shell structure as an impeller. This rotating part includes compressor and turbine blades connected by a hollow shaft structure, optionally with an internal blade structure that enhances the rotor dynamic performance and enables turbine cooling by ambient air suction through the shaft. Such a hollow shaft structure also contributes to reduced weight. The hollow shaft structure connecting the compressor and the turbine can also serve as a fuel driven hydrostatic bearing. Use of fuel as the hydro bearing support fluid instead of the commonly used oil, will allow for further reduction of the system complexity, and hence lowered costs. On the turbine side of the hydro bearing, a labyrinth seal may be used, in order to efficiently block flow of the fuel towards the turbine and thrust nozzle. The fuel from the bearing subsequently evacuates through a perforated medium towards the compressor-diffuser region and mixes as an aerosol with incoming air flow. In pursuit of reduction in engine size, a porous media combustor may be used to burn the premixed fuel-air mixture.

Porous media combustion is different from traditional combustion and has several advantages compared to conventional free-flame combustors. The surface area per unit volume of porous structure is very large, resulting in higher heat transfer between the fluid and solid phases. Moreover, small vortices produced by a solid porous formation causes highly turbulent inner flow, which intensifies momentum heat/mass transfer and ensures flame stabilization over wide range of flow velocities and equivalence ratios. Along with radiation and conduction, the porous media increases heat transfer from reaction zone upstream, preheating the incoming fuel-air gases and allowing decreased flame temperature, as a lower lean limit of fuel mixture is extended, leading to devaluation of NOx and CO emissions. A porous medium combustion chamber is particularly advantageous when an additive manufacturing method is being used to form the turbine, since such a porous medium acts as a self-supporting structure.

The rotating component of the engine is designed to be balanced after the manufacturing process through external ad hoc removal of mass from the surfaces. Imbalance is caused due to a centrifugal force created by uneven mass distribution, which shifts the shaft mass center away from the axis of rotation. Unbalance is measured in units of mass multiplied by its distance from the shaft axis. For a rigid body, the unbalance state can be fully defined by static unbalance, and couple unbalance, which results in dynamic imbalance. Static unbalance occurs when the principal axis of inertia is parallelly displaced relative to the shaft axis and can be simply corrected by a single mass correction placed opposite to the center of gravity. A couple unbalance is present when the principal axis of inertia intersects the shaft axis at the center of gravity due to two equal unbalance masses located at opposite ends of a rotor at antithetical positions. Correction of such unbalance will require at least two transverse correction planes as two masses need to be adjusted at 180-degree phase on each plane. Therefore, two balancing masses are considered, one in the area of engine intake and another in the engine nozzle. The axial position of such masses is not important as long as it can create force equal in magnitude but opposite in direction to the couple unbalance. Two accelerometers are typically attached to both surfaces to monitor vibrations during balancing procedure. Strobe light can be used to determine the phase angle of the unbalance. Combined readings of the strobe light and accelerometers provide the amount of unbalance and its angular position.

These described engines involve multidisciplinary optimization of aerodynamics, thermodynamics, heat transfer, rotor dynamics and stresses for turbomachinery and hydrostatic/dynamic bearing components under 3D manufacturing limitations. Although the performance of the described engines may be somewhat less than state-of-the-art microturbojets in terms of both thrust to weight ratio and thrust specific fuel consumption, due to the design constraints associated with their continuous printing method of manufacture, the expected disruptive change in cost and availability does indicate a significant market advantage for such products.

Such metal and ceramic additive pre-assembled manufacturing of single piece hollow compressor-turbine shaft and porous media combustion may be used to produce microturbojet engines through a single uninterrupted printing process. Uninterrupted pre-assembled printing of rotor-stator assemblies with internal hydrostatic bearings would significantly minimize costs. One such commercial application may be small-to-medium size unmanned aerial vehicles with disposable platforms that favor reduction in system and maintenance costs over maximizing performance metrics.

As described in co-pending PCT application No. PCT/IL2021/050007, for "Ultra-micro Gas Turbine Generator", having a common inventor and common ownership with the present application, because of the high temperatures generated in the turbine region, it is necessary to use a heat resistant ceramic material for constructing the rotary impeller. One suitable material is Silicon Nitride, which can withstand over 1200° C. Another ceramic material for construction of the rotary impeller, is zirconia, since it has lower heat conduction, enabling isolation of the heat of the turbine from the compressor and generator, both of which should be kept as cool as possible. Alternatively, a high-strength Nickel alloy, such as Inconel, Hastelloy, or similar can be used, as such alloys withstand high temperatures of over 1,000° C. while maintaining their strength. The methods of additive manufacturing described in the present application also enable the structures generated to be composed of different materials for different parts. Thus, it would be possible to form the gas turbine using a high temperature resistant material such as Inconel or the like, for the impeller, or at least those parts of the impeller in the turbine region that are exposed to the highest temperatures, and a less costly material, easier to print and sinter, for the parts of the engine that are not exposed to such high temperatures, such as the housing itself, thus further reducing the manufacturing costs. The additive manufacturing method described hereinabove, can be used to produce in a single manufacturing process, besides the gas turbine engines described above, any two-part device in which the inner part is totally enclosed within the outer part. This is achieved by printing the component layer-by-layer from the print plate upwards, with both the inner and the outer parts being generated together, one within the other, and layer after layer. A condition for the success of such a manufacturing process having self-supporting parts, i.e. parts without support struts between them, is that they have contours having a slope relative to the base plate plane, such that each printed layer can be supported only by the previously printed layers. The printed layer that is required to be self-supporting may include the weights of all of the layers printed above the layer being considered.

According to a further implementation described in this disclosure, there is provided another aspect of gas turbine engines, using at least part of the manufacturing methods and structure described hereinabove, relating to their use in mechanical respiratory ventilators, driven by gas pressure, to provide ventilator support for patients in respiratory distress. The use of gas pressure from a cylinder of compressed gas, to power the engine, provides the ability to use the ventilator in settings lacking the usual support facilities in a medical environment, such as a central compressed air supply or even lacking electricity or with unreliable electricity supplies.

A novel aspect of the presently describe ventilator motors, is the use the oxygen flow from a compressed supply cylinder, as used to provide supplemental oxygen to the patient, also as the power source for a gas turbine engine forming the motive force for the respiratory gases of the system. The engine has an impeller similar to that of a conventional gas turbine engine, but differs in that the motive force of the turbine is generated by a high velocity flow of the compressed oxygen through the turbine in order to generate high speed rotation. The turbine drives a centrifugal compressor or blower for generating the flow of the volume of air required for respiration of the patient. The airflow generated by the blower, can be mixed with the oxygen which exits the turbine, after providing the rotor with its rotational kinetic energy, and optionally also with additional oxygen from the oxygen supply, in order to increase the oxygen content of the respiratory air, as necessary. A set of valves as used in a conventional ventilator are then used to regulate the ventilation timing to the patient. This embodiment of the application therefore involves a ventilator blower system, based on a single combination turbine-blower impeller unit, which uses the oxygen supply from a compressed gas cylinder to provide the energy for its operation. In contrast, prior art ventilators generally use an electric motor driven blower to enable their operation.

Although the impeller can rotate within the housing on mechanical bearings, such as roller or ball bearings, it may be advantageous in such small gas turbine engines, because of the high speed of rotation at which the impeller rotates, to use hydro bearings to support the rotating impeller. According to another implementation of the ventilators of the present application, the hydro bearings can advantageously be supplied with compressed oxygen from the oxygen cylinder used for supplying motive forces to the gas turbine and for supplementing the oxygen content of the patient's air supply. By this means, the necessary external supplies necessary for the operation of the ventilator can be simplified, since the only gas required comes from a single cylinder of oxygen. In general, the oxygen used to propel the turbine is not at a sufficiently high pressure after exiting the turbine, as the support gas for the hydro bearings, and it is thus more useful for adding to the ventilator air supply, though its potential use for supplying the hydro bearings should not be negated.

There are several types of hydro bearings, including hydro-static and hydro-dynamic bearings. Hydrostatic bearings, which also include aerostatic bearings in the broader sense, where a gas is used as the support medium instead of a liquid, are machine elements in which the applied force is supported by liquid or gas film pressure. Such bearings are widely used to support various rotating parts, including in turbomachinery applications. Unlike hydrodynamic bearings, which produce fluid pressure by relative motion of two parts in a closed space enclosing the support fluid, the fluid in hydrostatic bearings, including both aerostatic and hydrostatic bearings, is pressurized by an external source. In such a bearing, the fluid film is present as long as external pressure is applied, independent of shaft rotating speed. Pressurized fluid is provided by an external source and enters the bearing at constant pressure through a restrictive orifice that is used to reduce the pressure if necessary. The flow passes through the bearing and leaves via a tiny gap between stationary and rotating parts, which restricts the flow of the fluid out of the bearing. The pressure built up inside this pocket acts against the applied load of the shaft and ensures separation of the surfaces, thereby maintaining proper positioning of the shaft. Hybrid bearings contain combined effects of hydrostatic and hydrodynamic bearing film pressure and they act as hydrodynamic bearings with a pressurized fluid (liquid or gas) supply. Both hydrostatic and hybrid bearings have high bearing film stiffness at low to zero speeds and high load capabilities at high speeds. Overall benefits of hydrostatic or hybrid bearings are: low wear, ability to support high shaft speeds, heavy loading capabilities, a large range of operating temperatures, high stiffness and damping, absence of friction at zero speed, absence of starting and stopping wear and suitability for additive manufacturing. In the present disclosure, and as claimed, the term "hydro bearing" is used to describe hydrostatic, hydrodynamic and hybrid bearings, driven by either gaseous or liquid fluid.

Both the gas turbine engine and the ventilator described operate based on the same technological principle—a thermodynamic process which converts energy encapsulated in the form of pressure, to shaft power through expansion in a turbine. Through a mechanical connection, a part of this shaft power is transferred to a compressor, which in turn converts a part of this energy to the pressure rise of a working fluid. In the scope of the present disclosure, a thermodynamic energy converter is used to described any device that consists of a mechanically connected compressor and turbine.

There is thus provided, in accordance with a first exemplary implementation described in the present disclosure, gas turbine engine comprising:

(i) a rotor comprising a turbine and compressor,
(ii) a housing that surrounds the rotor, the rotor being configured to rotate within the housing on at least one hydro bearing, the profiles of an outer surface of the rotor and the facing inner surface of the housing generating the surfaces of the at least one hydro bearing, (iii) a combustion chamber adapted for the combustion of a fuel/air mixture, and (iv) at least one channel adapted to direct combustion products from the combustion chamber to the turbine, wherein the housing and rotor are formed simultaneously and in a single procedure, with the rotor enclosed within the housing.

The single procedure may be an additive manufacturing procedure. Furthermore, formation of the housing with the rotor enclosed therein should be indicative of the gas turbine engine having been produced in an assembled form by an additive manufacturing procedure. The additive manufacturing procedure may comprise the deposition of a sequence of printed layers, and the angle which any part of the inner surface of the housing or the outer surface of the rotor makes with the plane of the printed layers, should be limited such that each layer is supported only by the previously printed layer. In any of the above described gas turbine engines, the rotor may be enclosed within the housing without internal supports between them.

According to further described implementations, in the above described gas turbine engines, the at least one hydro bearing may be any of a hydrostatic bearing, a hydrodynamic bearing, or a hybrid hydro bearing. Furthermore, the hydro bearing may be driven by a gas or a liquid.

These combustion chamber of these gas turbine engines may comprise a porous structure. Also, the housing may comprise at least one channel adapted to direct the fuel, prior to its entry into the combustion chamber, so as to provide the support medium for the at least one hydro bearing. Such a flow of the fuel through the at least one hydro bearing is adapted to provide cooling to the rotor. Additionally, the flow of the fuel through the at least one hydro bearing is adapted to increase the temperature of the fuel prior to its passage to the combustion chamber. The flow of the combustible fuel through the at least one bearing may also atomize the fuel prior to combustion. Finally, the combustion chamber may be formed within the housing, or may be disposed external to the housing.

In any of the above described gas turbine engines, at least the turbine region of the rotor may be formed of a material capable of withstanding higher temperatures than the material of which the housing is formed.

According to further embodiments described in the present disclosure, there is provided a method of forming a gas turbine engine, comprising:

(i) using an additive manufacturing process to form a rotor comprising a turbine and a compressor, and a single piece housing, the rotor being formed inside the single piece housing, and the rotor being configured to rotate within the housing on at least one hydro bearing whose surfaces are generated between an outer surface of the rotor and a facing inner surface of the housing, and (ii) providing a combustion chamber for the combustion of a fuel/air mixture, and at least one channel to direct combustion products from the combustion chamber to the turbine.

In such a method, the combustion chamber may be formed within the housing as part of the additive manufacturing process.

According to a further implementation of these methods, the rotor and the housing should have a common planar end surface perpendicular to the rotor axis of rotation, that surface being in contact with a printing base plate during the additive printing process. The rotor and the housing may be printed in layers from the common printing base plate. Additionally, the angle between the outer surface profile of any part of the rotor or the inner surface profile of any part of the housing and a plane parallel to the printing base plane should be sufficiently large that every layer formed by the additive printing process is supported by the previously formed layer. In such a case, the angle is such that any overhang of a formed layer over the preceding formed layer has sufficient strength to be self-supporting.

According to yet further implementations described in the present disclosure, there is provided a ventilator blower assembly, comprising:

(i) a rotor comprising a turbine and a compressor, such that the rotation of the turbine generates rotation of the compressor, (ii) a housing surrounding the rotor, (iii) at least one bearing configured to enable the rotor to rotate within the housing, (iv) an inlet channel adapted to direct a pressurized stream of oxygen from an external source, over the blades of the turbine, (v) air inlet and outlet passages positioned such that the compressor, when rotating, is adapted to force air ingested through the inlet passage through the outlet passage, and (vi) at least one additional passage adapted for adding the oxygen exhausted from the turbine to the flow of air ingested through the inlet passage.

In such a ventilator blower assembly, that at least one additional passage adapted for adding the oxygen exhausted from the turbine to the flow of air ingested through the inlet passage may be either part of the housing, or may be a separate conduit.

Such a ventilator blower assembly may further comprise an inlet port adapted for the direct addition of oxygen from the supply of compressed oxygen to the flow of air ingested by the blower. Furthermore, the at least one bearing may be a hydro bearing. In such a case, the ventilator blower assembly may further comprise internal channels in the housing which direct a gas flow into the at least one hydro bearing, to support the rotor when rotating. The internal channels for the hydro bearing may be configured to be connected to the source of the pressurized stream of oxygen. Additionally, the flow of oxygen for the hydro bearing may be used to cool the rotating rotor.

In any of the above mentioned ventilator blower assemblies, the rotor and housing are produced in an assembled form by an additive printing method. Furthermore, the rotor and housing may have a common planar end surface perpendicular to the rotor axis of rotation, that surface being adapted to be in contact with the printing table during the additive printing process.

Finally, in the above described ventilator blower the rotor may be powered only by the pressurized oxygen supply.

According to yet further implementations described in the present application, there is provided a method of providing respiratory ventilation to a subject, the method comprising:

(i) inputting a supply of compressed oxygen to a turbine of a gas turbine engine, the turbine being part of a rotor on which are connected to the blades of a blower, such that the rotating turbine rotates the blower blades, the blower being adapted to ingest air for delivery to the subject, and (ii) mixing the oxygen after ejection from the turbine, with a flow of air ingested by the blower, such that oxygen supplemented air is supplied to the subject.

Such a method may further comprise the step of supplying compressed oxygen to at least one hydro bearing for enabling rotation of the rotor within a housing of the gas turbine engine, such that the compressed oxygen also serves as the support medium of the at least one hydro bearing. Such methods may further comprise the direct addition of oxygen from the supply of compressed oxygen to the flow of air ingested by the blower. Finally, the method may further comprise the step of regulating the ventilation timing to the subject by use of a set of controlled valves.

Finally, there may be a number of locations throughout this disclosure, where different nomenclatures may have been used to describe the same feature, and may also have been claimed thuswise. Some such instances include the alternative naming of the impeller of the gas turbine engine as the rotor, and vice versa. Similar situations arise also in the naming of the additive manufacturing process as an additive printing process, since it is generally understood that the most commonly used additive method is that of printing the successive layers. Furthermore, reference is made to what is commonly called the action of a gas in generating rotation of a turbine, when a more accurate language would refer to the action of a gas in generating rotation of the turbine blades. Such alternate nomenclature is not generally intended to imply patently different functional parts, and is not intended to limit the meaning or scope of any claimed features.

BRIEF DESCRIPTION OF THE DRAWINGS

The presently claimed invention will be understood and appreciated more fully from the following detailed description, taken in conjunction with the drawings in which:

FIG. 1A shows a schematic representation of an exemplary oxygen powered ventilator system for providing a suitable air-oxygen mix to a patient being ventilated, while

DETAILED DESCRIPTION

Figure 1A:
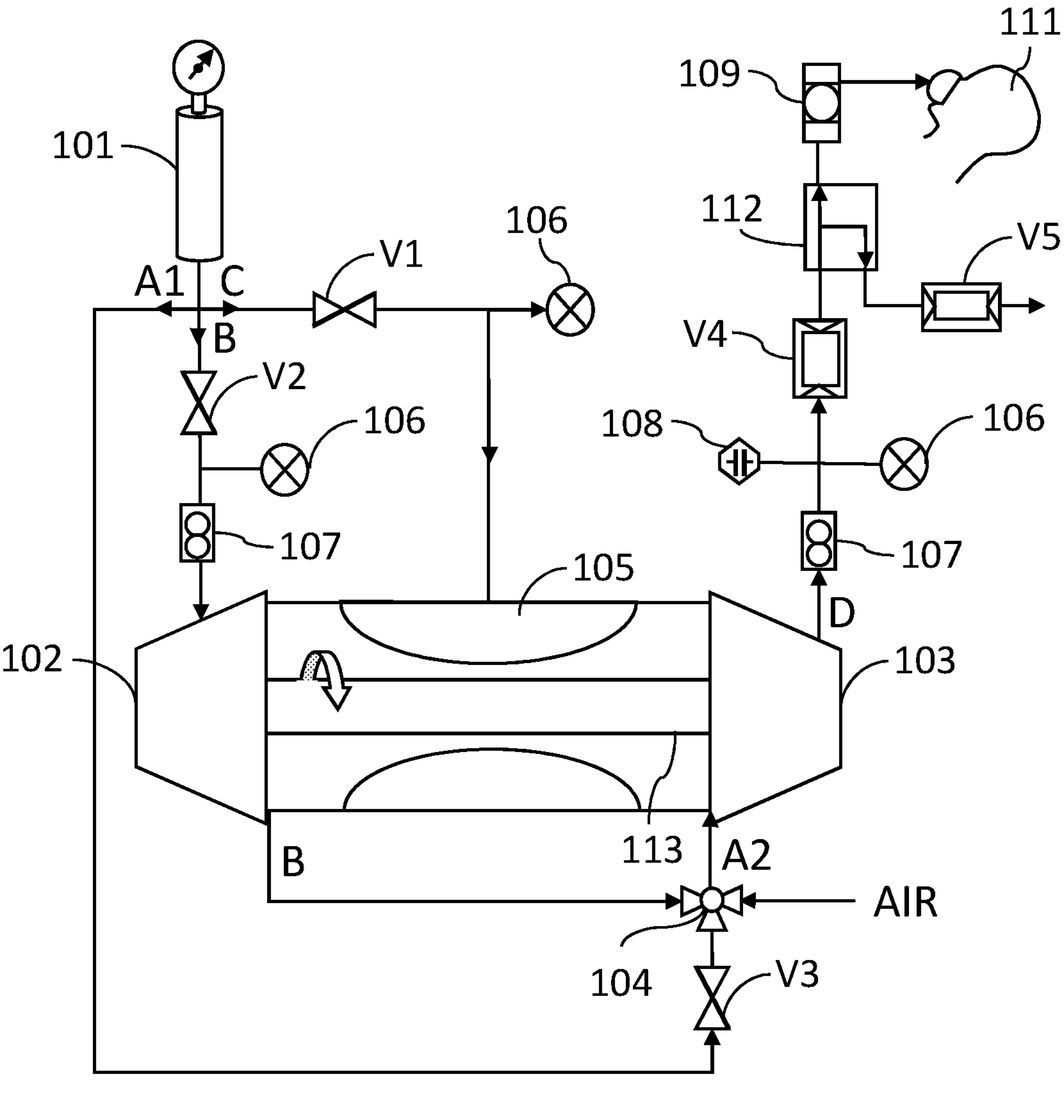
Figure 1B:
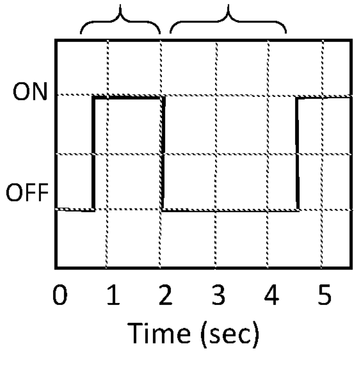
FIGS. 1B and 1C show graphs of the inspiration and expiration cycles of the system.
Figure 1C:
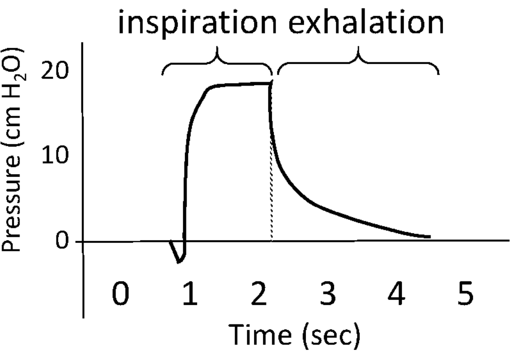

Reference is now made to FIGS. 1A to 1C, which illustrate in FIG. 1A, a schematic representation of an exemplary mechanical ventilator system for providing a suitable air-oxygen mixture to the patient being ventilated, according to one exemplary implementation in the present disclosure, and in FIGS. 1B and 1C, the cycle of mechanical ventilation provided by the system. The disclosed mechanical ventilator differs primarily from previously available ventilators in that the blower is powered by the compressed oxygen which is also used to provide oxygen to the patient being ventilated. In the example system shown in FIG. 1A, the oxygen supplied from a compressed oxygen tank 101 is used for up to three separate functions:

(i) A first function, shown by branch A, is to supply supplemental oxygen for mixing with the air supplied to the patient 111 being mechanically ventilated, as is usual in conventional ventilator systems.

(ii) The primary function, through branch B, is to power a turbine 102 used to rotate the compressor or blower unit 103 of the ventilator.

(iii) A third, and optional function is to provide, through branch C, the hydrodynamic flow of compressed gas to hydro bearings 105 which support the rotating impeller unit of the ventilator.

In branch A1, oxygen from the tank is fed via a valve V3 into a manifold 104 which combines the oxygen with ambient air, and channels the air-oxygen mixture through branch A2 into the centrifugal compressor or blower 103, which is driven by the turbine 102. From this point onwards, the air-oxygen mixture can be handled by a number of different flow control arrangements, a typical but non-limiting example being shown in route D. The blower directs the air-oxygen mixture via route D, through a flowmeter 107, past an oxygen sensor 108 and a pressure gauge (up to 2000 Pa) 106 to determine the flow and relative amount of oxygen going to the patient. After passing through one-way valve V4, the regulated air-oxygen mixture passes through a selector 112, which determines the cyclic intervals, typically from 1 to 4 seconds, at which the flow of gas will be directed to the patient. After passing through a filter 109, the gas mixture will be administered to the patient 111. During the times when the gas is not directed to the patient, i.e., during the expiratory phase of the respiratory cycle, the expired carbon dioxide from the patient is routed through one-way valve V5 to the environment.

FIGS. 1B and 10 are exemplary graphs illustrating the timing of the mechanical breaths provided to the patient 111 using the selector on/off switch 112 of FIG. 1A, and the resulting respiratory trace of the mechanical breath provided is shown in FIG. 10, in which inspiratory and expiratory phases of the respiratory cycle are shown.

Referring back now to FIG. 1A, in branch B, according to one exemplary arrangement, compressed oxygen is directed through valve V2 and is monitored by a pressure gauge 106, typically up to 4 bar, before being passed through a flow meter 107. The pressurized oxygen is then used to power a turbine 102, which is used to turn the compressor 103, the compressor and turbine being connected by an impeller structure or shaft 113. After providing the motive force for operating the blower or compressor 103, the oxygen gas can advantageously be directed through manifold 104 to be added to the air flow supplied to the patient, such that it is not wasted after performing its primary energy providing function. The impeller may, according to another advantageous implementation, be supported by a hydro bearing to enable it to rotate at high speeds, and this hydro bearing can use compressed oxygen supplied through branch C. The compressed oxygen passes through valve V1, is monitored by a pressure gauge, typically up to 4 bar, and is used to provide the fluid support for the hydrodynamic hydro bearing 105. The oxygen used to provide hydrodynamic support of the hydro bearings may subsequently be fed into the manifold 104 for routing to the patient, such that it too does not go to waste.

Such a ventilator system may have a compressor flow rate of 250 L/min (5 gr/s); oxygen enrichment of 50-80%; a turbine flow rate of 1.5-3 gr/s; a rotation speed of 36,000 RPM; and one way valves to prevent backflow. The pneumatic oscillatory valve may have a 1-4 second on/off cycle to simulate breathing. The described system of valves, flow meters, oxygen sensors, and tubing are shown for a typical, non-limiting implementation, and other configurations may equally well be used in other applications of the system.

Figure 2:
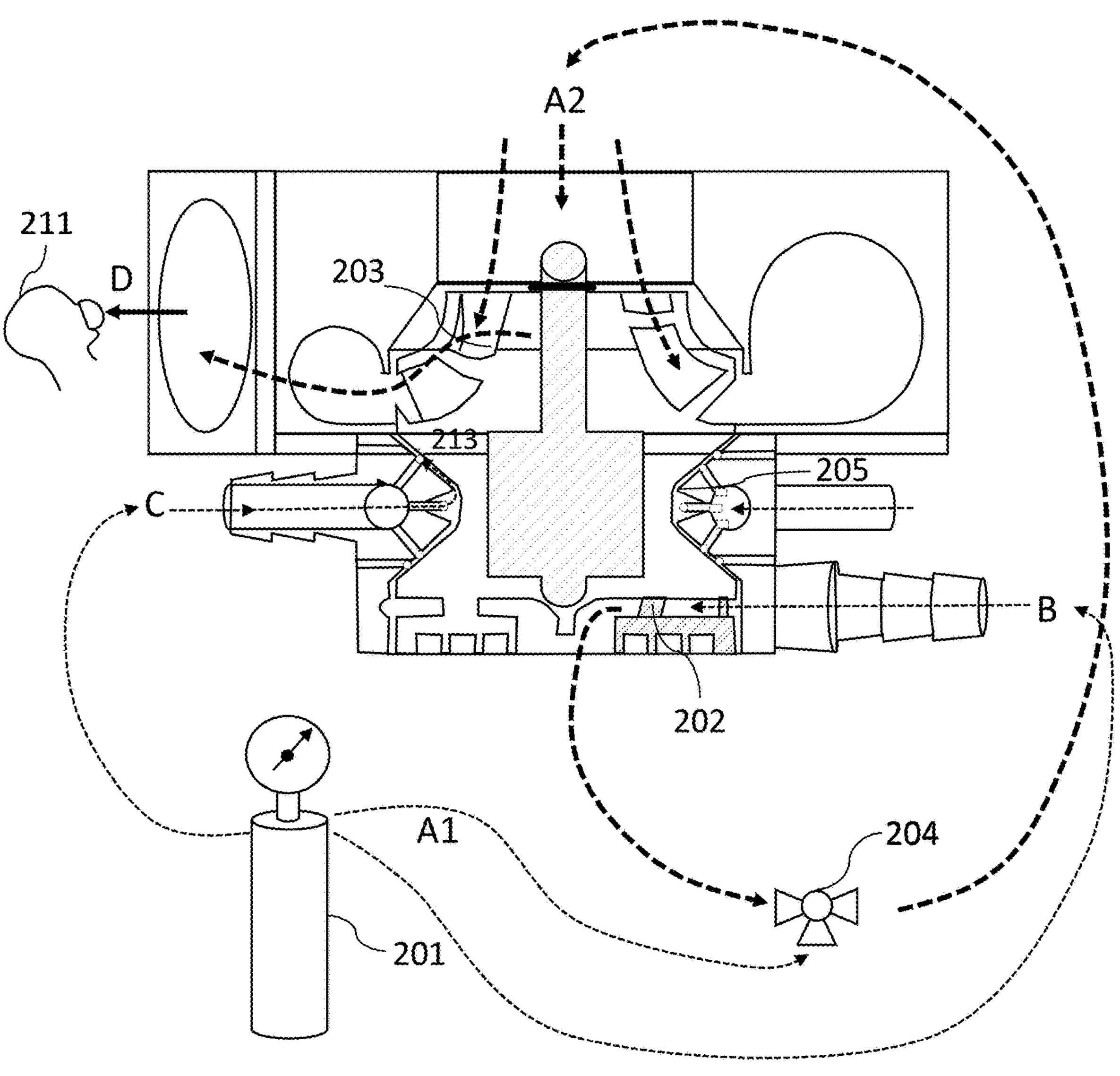
FIG. 2 shows a cross-sectional view of the complete blower assembly mechanism in an exemplary use for ventilation of a patient.

Reference is now made to FIG. 2, showing a cross-sectional schematic view of a typical implementation of the disclosed ventilator system, highlighting important mechanical features and the flow of air and oxygen through the device. The finely dashed lines show the flow of high pressure gas, while the thicker dashed lines generally show the flow of low pressure gas. As in FIG. 1A, the compressed oxygen used to power the turbine-compressor unit may be provided from a high pressure cylinder 201 into inlet B, and is used to power the turbine 202. Rotation of the turbine turns the impeller 213, with the compressor or blower 203 at its opposite end, which draws in air via inlet A2. The oxygen exhaust from the turbine is channeled via the manifold 204 to the blower 203, also via inlet A2, and the regulated air-oxygen mixture is provided to the patient via outlet D. Compressed oxygen from the oxygen tank 201 is also routed through inlet C to the hydro bearings 205. As mentioned above, the components of the turbine engine may be additively manufactured using a standard three-dimensional printer. The process is easily scalable for the turbomachinery components, hydro-static bearings, and housing. The controls and one-way valves, filter, pressure and oxygen sensors may be supplied as commercial off-the-shelf parts. Variable characteristics of the device comprise a breathing rate controlled by an oscillating valve at 15-60 breaths/min. Air flow rate may vary between 200-350 L/min, which can be adjusted by a controllable valve. Breathing pressure is controllable between 10-30 cm $H_2O$. Oxygen saturation may be controlled by an oxygen supply valve that enables the supplemental oxygen to be 0-100% of incoming air.

Advantages of such an implementation are that the device requires no electrical power supply, no lubrication, and no assembly, as it may be fully additively manufactured ready to use. The mechanical ventilator uses only the pressure from the oxygen supply tank to power the ventilator, the used oxygen then being rerouted back to the patient, thus conserving the oxygen for its usual use. Further, using an additive manufacturing approach allows the rapid production of simple and cheap automatic ventilation units. Such units can be used in case of emergency to provide critical lung ventilation for patients who might otherwise be unable to receive adequate treatment. Although missing non-essential features such as temperature and humidity control, implementations of the disclosed ventilator system provide the most critical functionality to save lives, i.e., automatic oxygen saturation for patients in respiratory failure.

Figure 3:
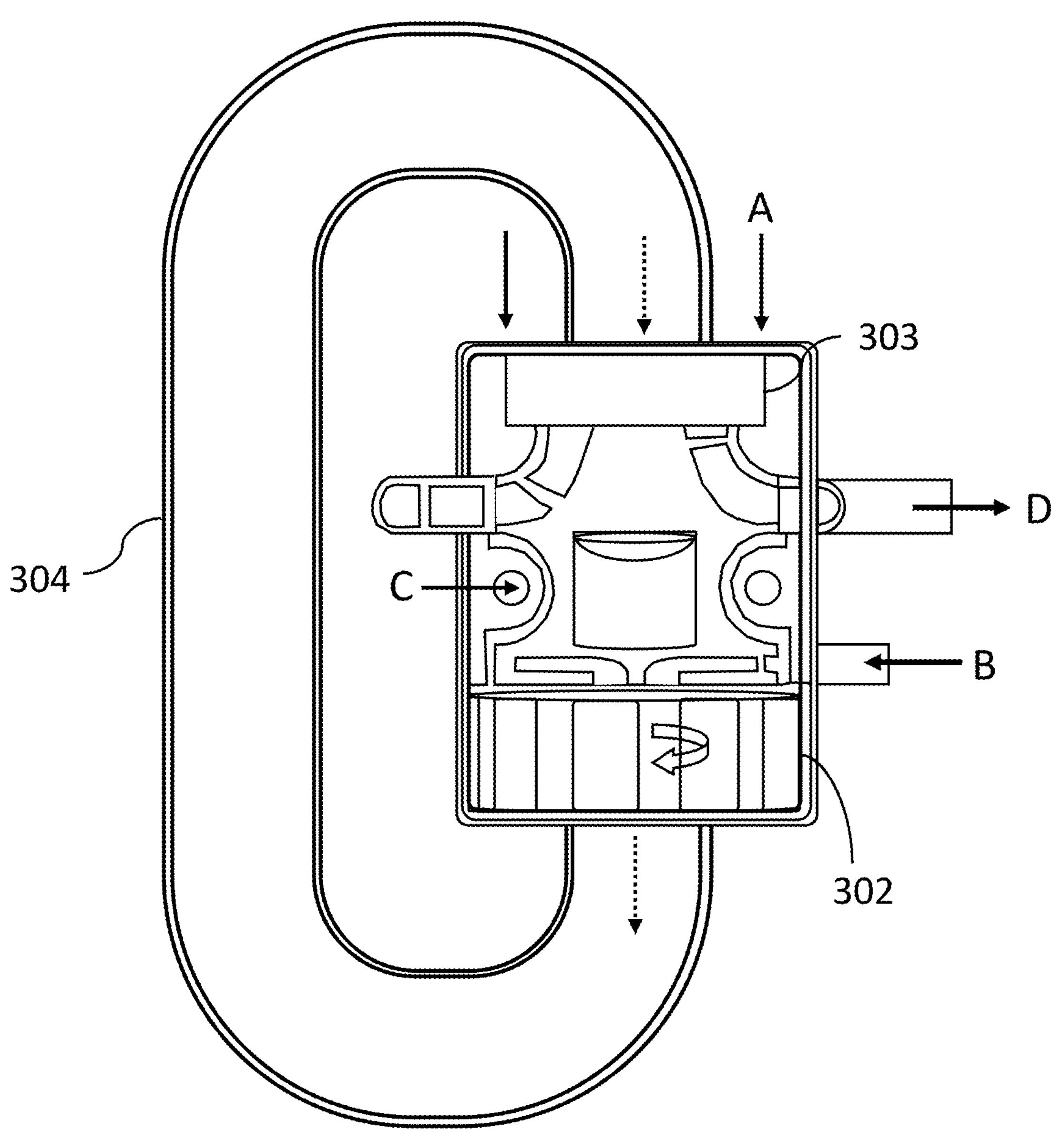
FIG. 3 shows the air and oxygen flow paths used to power the blower, with the air intake and outlets of the blower assembly having an attached air manifold.

Reference is now made to FIG. 3, illustrating an alternative schematic representation of the mechanical ventilator of FIGS. 1A and 2, showing how the compressed oxygen flow B, expended from the turbine 302 after providing the turbine with its rotational energy, is routed back into the blower 303 through passageway 304, shown schematically as the input manifold feature 104 in FIG. 1A, and feature 204 in FIG. 2, where it is mixed with the air intake A, for enriching the oxygen content of the ventilator air flow. This oxygen-enriched air flow is then provided to the patient though port D.

Figure 4A:
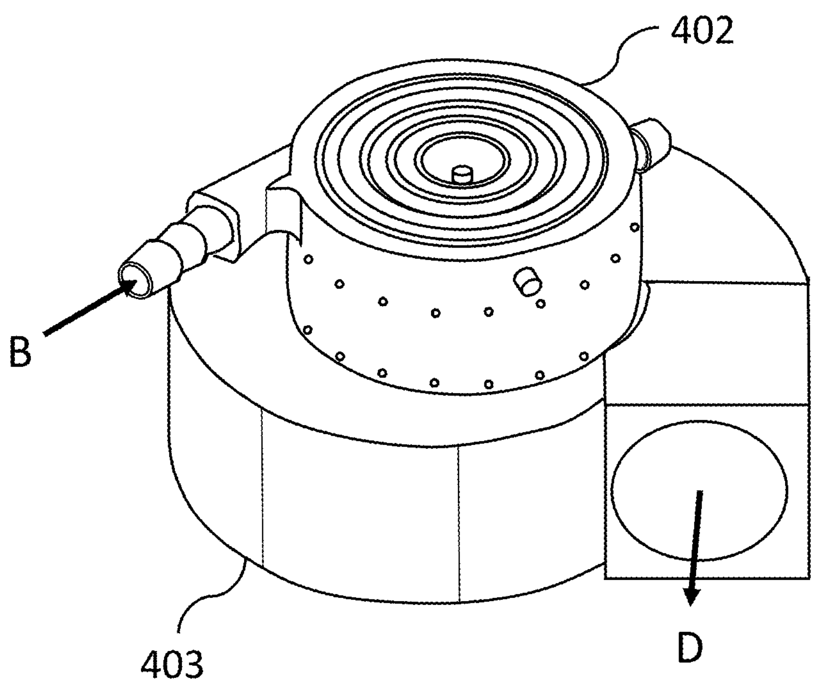
FIGS. 4A and 4B show isometric views of an exemplary assembled ventilator blower assembly, as viewed from the turbine end (FIG. 4A) and from the blower end (FIG. 4B)
Figure 4B:
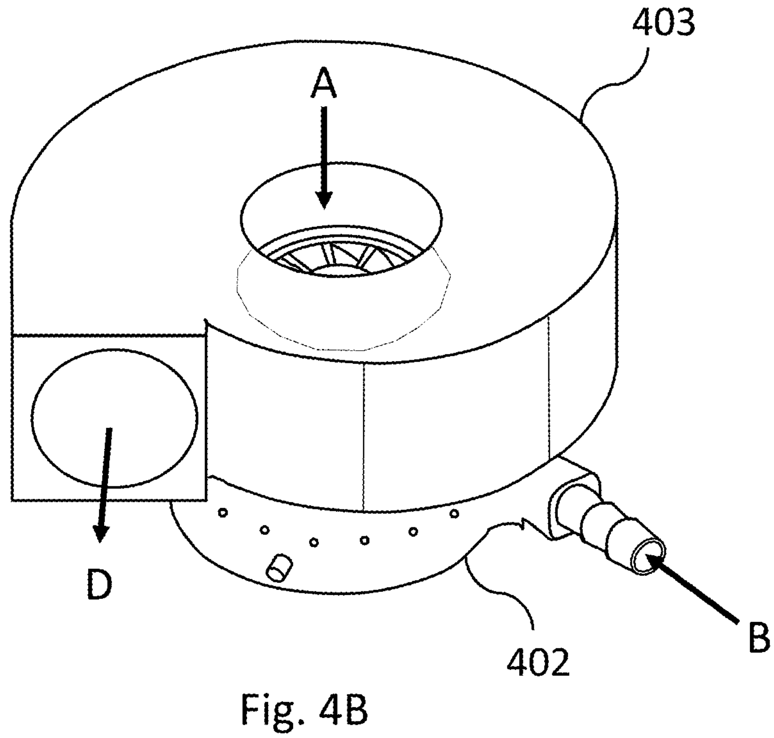

Reference is now made to FIGS. 4A and 4B, illustrating external views of the ventilator turbine-compressor unit from the turbine end 402 (FIG. 4A), showing the pressurized oxygen input port B, and from the blower/compressor end 403 (FIG. 4B) of the motor unit, showing the air intake A to the blower, and the regulated air/oxygen mixture output D to the patient. The endcap illustrated in FIGS. 5A to 5D, not shown in FIG. 4A or 4B, would be fitted over the end of the turbine 402.

Figures 5A, 5B, 5C, 5D:
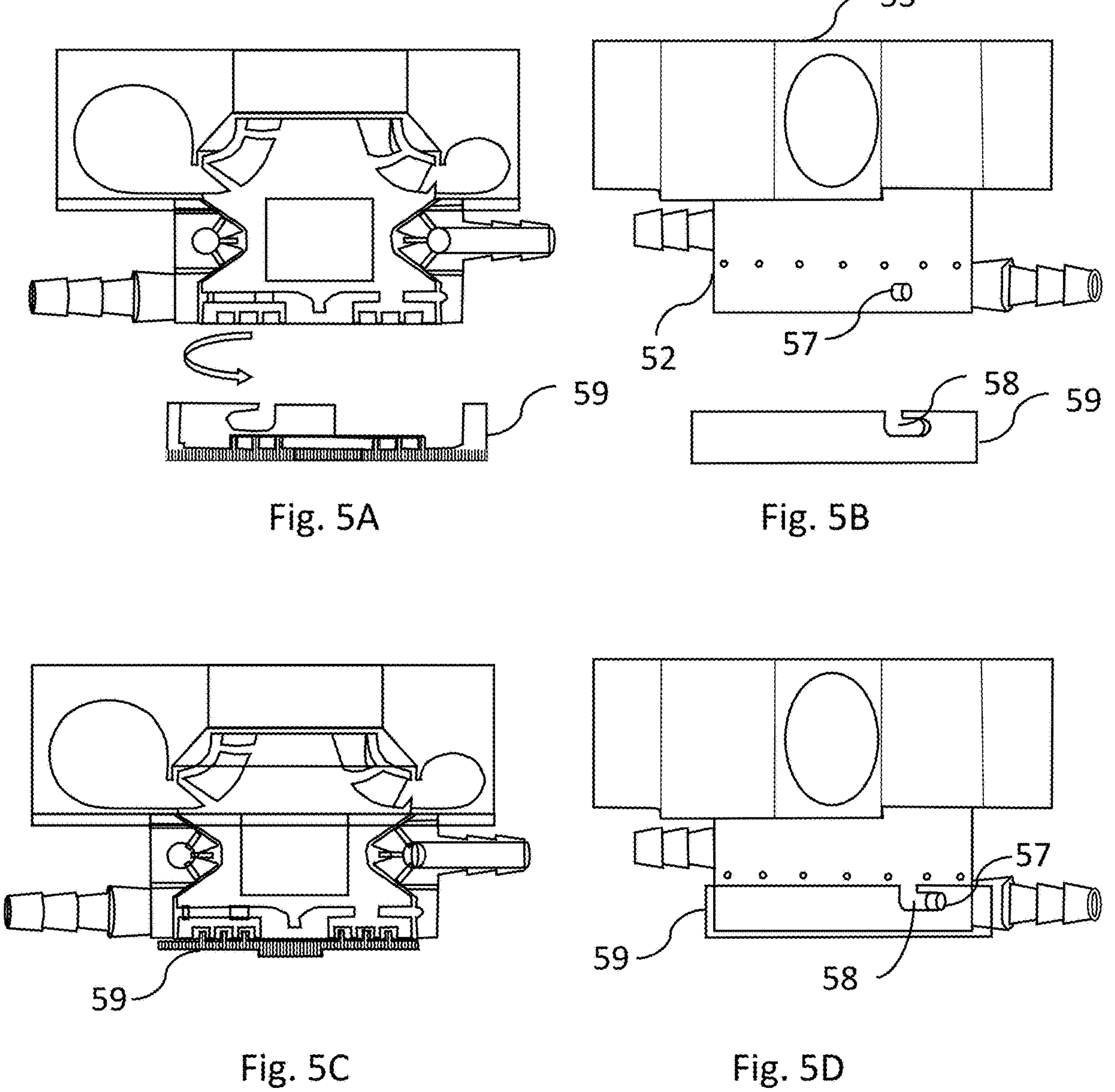
FIGS. 5A and 5B respectively show cross-sectional and side views of an exemplary ventilator blower unit, without an end-cap attached, while FIGS. 5C and 5D respectively show cross-sectional and isometric views of the exemplary ventilator blower unit of FIGS. 5A and 5B, with an end-cap attached.

Reference is now made to FIGS. 5A to 5D, illustrating the design and fitting of an endcap 59 for the ventilator rotor-stator turbine-blower assembly. The endcap is shown as a separate element, but it too may be additively manufactured as an integral part of the housing with the impeller inside. FIGS. 5A and 5C show cross-sectional views of the ventilator assembly, and FIGS. 5B and 5D show a side view of the assembly. In FIGS. 5A and 5B, the endcap is shown in position ready to be mounted onto the turbine 52 end of the ventilator engine, being secured in this exemplary construction by a pin 57 and groove 58 arrangements, which locks the cover on by means of a slight turning motion. Closing the end of the turbine prevents escape of the oxygen after it has performed its motive task, so that it can be added to the ventilation air flow. In FIGS. 5C and 5D, the endcap is shown in place after attachment.

Figure 6:
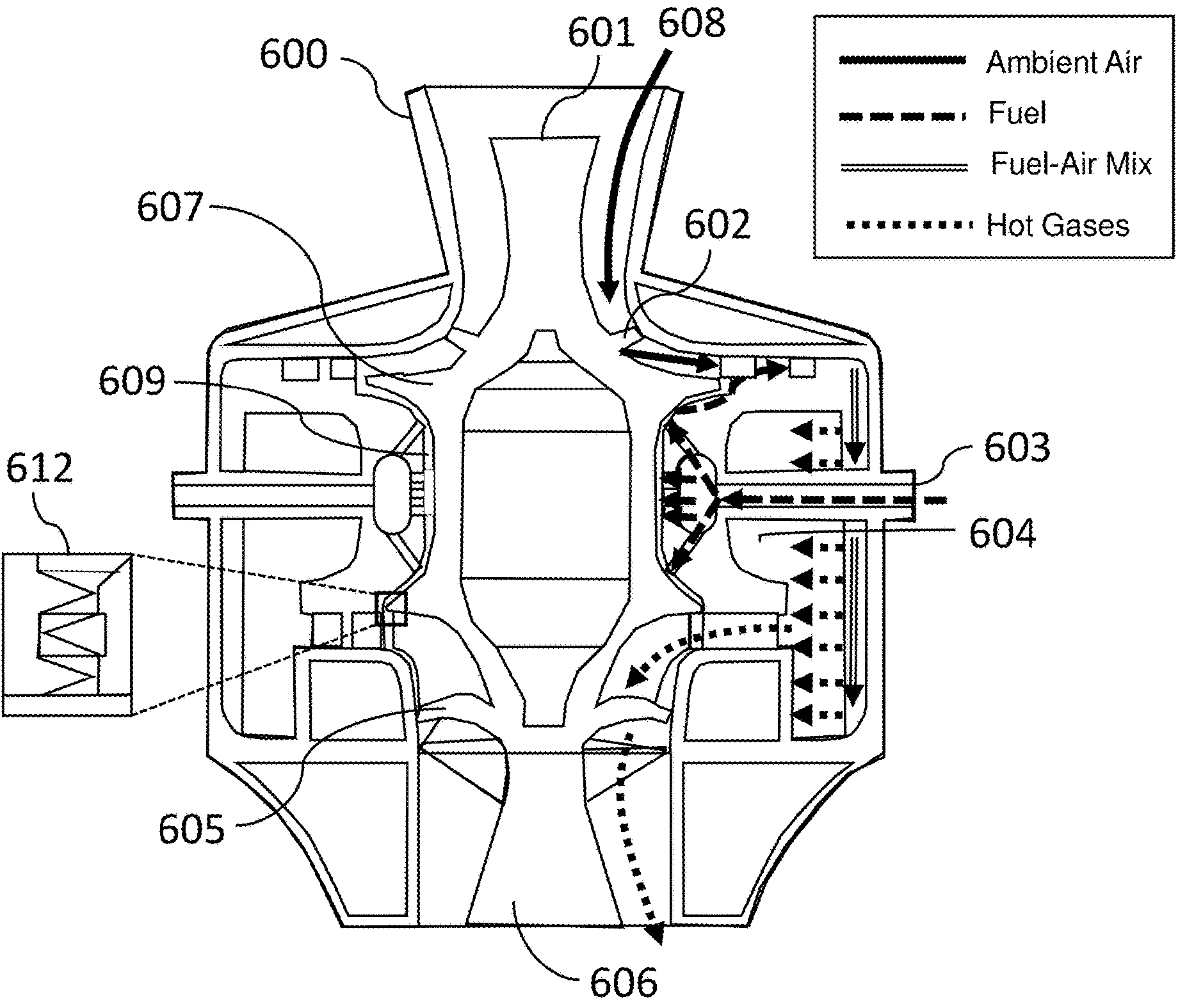
FIG. 6 is a schematic cross sectional drawing of a gas turbine engine of the present disclosure, in which the gaseous fuel used to power the engine also supplies the gas of an hydro bearing assembly.

Reference is now made to FIG. 6, illustrating another exemplary implementation of the present disclosure, showing a turbine-compressor rotor-stator assembly used in a gas turbine engine, such as may be employed to power an unmanned aerial vehicle or drone. This differs from the ventilator engine shown in FIGS. 1A to 5D, in that the motive force for the turbine comes from the combustion gases of a fuel-air mixture, instead of from the flow of compressed oxygen from an oxygen cylinder, or another compressed gas. The gas turbine can then be used to provide thrust, rather than just rotational energy to a ventilator blower. The targeted application may be to provide thrust to small-to-medium size UAVs, including disposable platforms. Currently small to medium UAVs are commonly powered by micro-gas turbine engines that cost from 30,000 to 150,000 USD, involving numerous parts and manufacturing methods in a lengthy process. This complicated process inflates the costs of both disposable and reusable platforms. In multi-mission platforms, significant efforts are invested towards prolonging service life as maintenance becomes increasingly important and costly. The present disclosure shows a low cost engine, which has the advantages of being produced through additive manufacturing in its final topology using a single simultaneous, uninterrupted printing process for both rotor and stator, thereby eliminating assembly costs. A typical sized engine for powering a small UAV could have a diameter of up to 30 cm, a thrust rating of 650 N and an air mass flow rate of ~1.4 kg/s, though it is to be understood that these specifications are not intended to be limiting.

Production of the engine through additive manufacturing enables reduction of components to just two parts—a static casing 600 with an embedded impeller 607, in the form of a shell structure, completely enclosed within the outer casing 600. The rotating shell structure includes the compressor end 601 with its blades 602, and the turbine end 606, with its blades, 605. This construction enhances rotodynamic performance. The impeller of the engine is supported on hydro bearings 609, which support the high rotational speed impeller 607. Use of hydro bearings provides low friction and absence of wear, and the ability to support large loads. The hydrostatic bearing should also provide radial and axial support of the internal rotating impeller. Additionally, such a hydro bearing construction is compatible with the additive manufacturing method used to form the impeller and housing in one process, with the bearings per se, inbuilt during construction. However, the hydro bearings used in the present engine differ from those conventionally used, in that the support gas is not air, but the fuel used to power the engine. The fuel enters at port 603, and is first directed to the hydrostatic bearings 609. The use of the fuel flow in the "air" bearing has an additional benefit that would not arise from the conventional use of air. In addition to the cooling effect which the fuel flow has in the bearing, removing heat from the impeller, an additional advantage is that the heat removed from the bearing is used to preheat the fuel before combustion, thereby assisting in the fuel atomization, and enhancing the efficiency of its combustion by improving the thermal output available from the fuel.

After providing the support for the high speed rotating impeller, the fuel then mixes as an aerosol with incoming air 608, input by the compressor 601, 602. The combustion chamber 604, advantageously having a porous medium to ensure complete and efficient combustion, is used for combustion of the premixed fuel-air mixture. The hot combustion product gasses then pass through the turbine 605, 606, thereby generating the power for operating the compressor 601, 602 to provide a copious intake of air. The hot gasses then exit the turbine end 606 of the engine, generating the thrust desired from the engine in the case of a jet engine, or exhausted in the case of a power generating gas turbine engine. The inner rotating impeller component may be balanced after manufacture through external removal of mass from specific surfaces, to produce a rotating system that balances out centrifugal forces.

Figure 7:
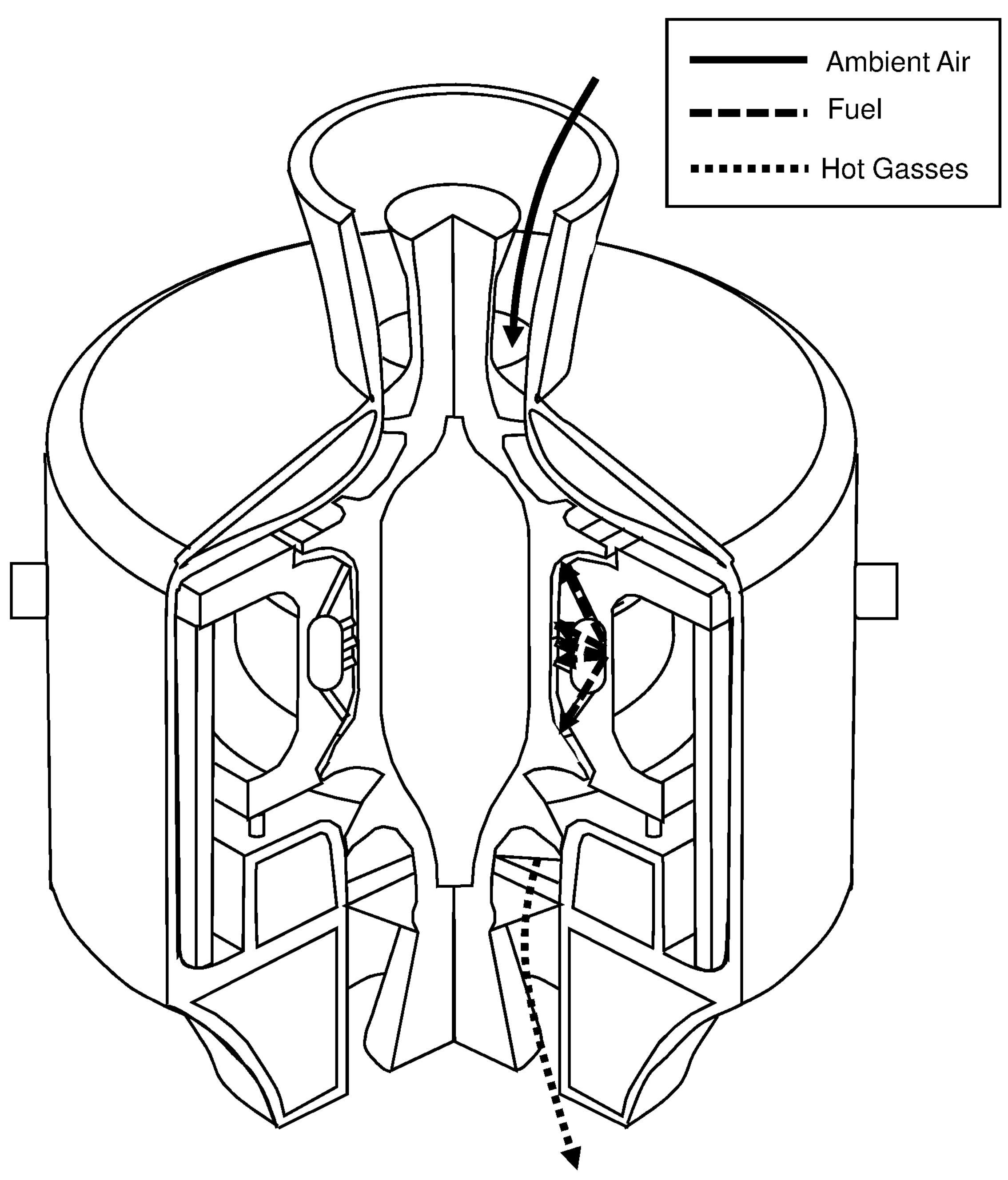
FIG. 7 is a cut-away isometric drawing of the engine of FIG. 6.

FIG. 7 is a cut-away isometric view of the engine of FIG. 6, showing more clearly the internal structure and the flow path of the fuel and hot gasses.

In the implementation of the gas turbine engine shown in FIGS. 6 and 7, the combustion chamber 604 is shown as being formed within the static casing or housing 600 of the engine. Besides such a structure, gas turbines and jet engines can alternatively have their combustion chambers embodied or attached externally to the engine housing, and such a structure can also be used for the presently described engines. When the combustion chamber is external to the housing, the pressurized air 608 from the compressor 601, 602, is ducted out of the housing 600 to an external unit (not shown in the drawings) where the combustion takes place inside that external combustion chamber. The hot and pressurized combustion product gasses are then ducted back into the housing 600 into the passageway(s) which direct the gas stream onto the turbine blades 605. In the same way as is shown in the gas turbine engine with an internal combustion chamber 604 of FIGS. 6 and 7, the turbine 605 drives the compressor 601, 602 and the remaining energy of the thermodynamic cycle can be converted to shaft power, or to kinetic energy at the exhaust 606. It should be noted that even with an external combustion chamber, the fuel may be first channeled through the hydro bearing 609 of the engine to provide the support medium therefor.

Figure 8A:
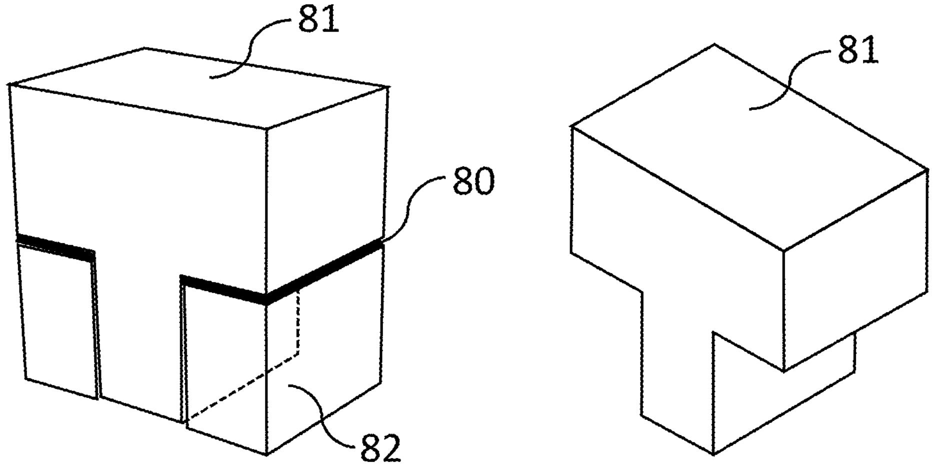
FIGS. 8A and 8B show schematically how the supportless additive printing of one part totally enclosed within the other can be performed.
Figure 8B:
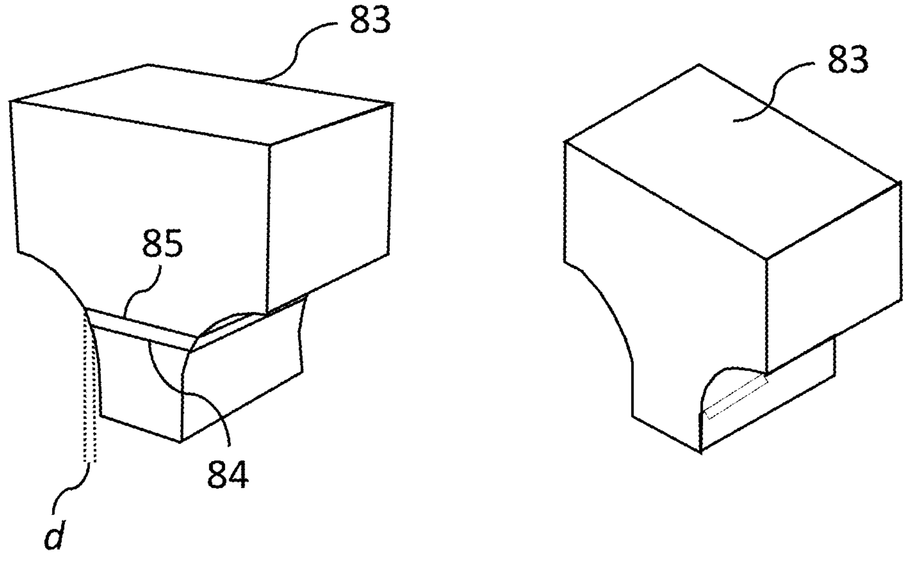

Reference is now made to FIGS. 8A and 8B, illustrating the principle of support-less additive manufacturing. In additive manufacturing, each layer is supported by the previously printed structure. Typically, three-dimensional printed objects are based on printing one layer at a time, each subsequent layer building on the previous one. When such a process is used to print an object 81 with upper layers having components that extend beyond the previously printed lower layers, as shown in FIG. 8A, current methods require the use of a temporary supporting structure 82 to provide a frame for the extension of the upper layer outwards beyond the lower layer. This temporary supporting structure will be removed, as described below, once the part has been completely produced. Additive manufacturing enables simultaneous printing of two interconnected components, e.g., in which a smaller piece fits inside a larger piece, by printing the component layer-by-layer from the print plate upwards. Thus, both the inner and the outer parts are generated together, one within the other. Current use of three-dimensional printing for concentric parts, however, is limited to items printed having non-enclosed spaces, having an opening for removal of the internal supporting structure 82, as otherwise the temporary structure 82 necessary to support the inner component remains enclosed inside the completed outer component.

Reference is now made to FIG. 8B, which illustrates a support-less method enabling the generation of completely enclosed integrated co-axial structures. The method is based on the design of the internal part having a gradient between successively printed layers sufficiently small that each layer may be supported only by the previously printed layer. By designing the parts in this manner, the need for internal support structures is eliminated. The parts designed may need to have some compromise properties over an ideal design, because of the limitations to the part profiles that may be used, but the savings thus generated by this method of additive manufacturing of integrated structures should provide an overall positive stimulus for the method for those applications where a satisfactorily functioning component may be produced using this method. Referring now to FIG. 8B, the prior art part 81 of FIG. 8A, has been redesigned as part 83, having a base section leading into the upper section by means of a sloped profile, instead of a right angled profile. The design of the sloped profile, which could be curved, as shown in FIG. 8B, or having straight line gradients, should be such that the overhang, d, of one layer 85 over the previously printed layer 84 should be no larger than the distance for which the strength of the printed layer 85 enables the layer 85 to remain self-supported. The allowed gradient should be calculated according to the mechanical properties of the material being deposited, and of the thickness of the layers being printed. Designs such as that shown in FIG. 8B minimize post-processing and enable the construction of mutually rotating surfaces of a stator and impeller to be printed together simultaneously, and without any internal supporting struts.

A method of designing an integrated composite structure having a movable inner part produced while entirely confined within an outer static housing, may thus be proposed by first defining the base plane of the composite structure, from which the printer will generate the entire structure. The spatial orientation of this base plane also defines the geometrical orientation of the subsequently printing layers superior to the base plane. The strength of a printed layer of the material being used to build the structure is then calculated, where the stiffness of the layer is determined using the Young's modulus of the material, and the thickness and width of each incremental printed layer. This will enable a calculation to be made, using the extent of bending that will be expected for the overhang of a single superior printed layer of the material, beyond the inferior layer previously printed. This maximum overhang will be dependent on the strength of the material being printed, the thickness of the layer being printed, and the sag of the overhang allowable for the part being produced. A permitted maximum level of bending should be defined, which will be determined according to the designed shape of the structure being produced. It is assumed that once a specific layer has been printed, the weight of successive layers printed vertically on top of it will not generate additional bending, since although the bending moment will be larger because of the additional gravitational forces, the layers thus produced will have a substantially increased strength because of the increased structural thickness.

A simplified method of determining the allowable overhang is to calculate the bending expected in a section of the printed layer, supported at one end by the layers below it, and experiencing a distributed force along the overhang length because of its weight. If the overhang were to be considered a cantilever beam, supported at one end, its bending d would be given by:

$$d = \frac{FL^3}{3EI}$$

where d is the deflection at the outer extremity of the overhang

F is the force applied at the extremity of the overhang

L is the length of the overhang

E is the module of elasticity of the material

I is the second moment of inertia of the overhang.

Though this is a very simplified model for the calculation of the overhand bending, mainly because the force is applied along the length of the overhang rather than at a point at its outer extremity, it enables an approximate calculation of the bending to be made. Thus, the deflection is seen to be proportional to the third power of the length of the overhang, such that the allowed extent of the overhang is highly dependent on the deviation that would be allowed of the shape of the layer from the intended shape Once that criterion has been determined, it then becomes possible to determine the minimum angle from the horizontal that the profile of the structure being printed can accommodate, since at any angle less than that minimum allowed angle, the bending of the unsupported edges of a print layer may result in the shape of the structure departing from the intended shape by more than an allowed level.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

I claim:

1. A gas turbine engine comprising:

a single piece rotor comprising a turbine and compressor;

a single piece housing that encloses the single piece rotor, the single piece rotor being configured to rotate within the single piece housing on at least one hydro bearing, profiles of an outer surface of the single piece rotor and an inner facing surface of the single piece housing generating surfaces of the at least one hydro bearing; and a combustion chamber adapted for the combustion of a fuel/air mixture for providing combustion products to the turbine, wherein the single piece housing further comprises at least one channel adapted to direct fuel, prior to its entry into a combustion chamber, through the at least one hydro bearing such that the fuel provides a support medium for the at least one hydro bearing.

2. A gas turbine engine according to claim 1, wherein the single piece rotor is enclosed within the single piece housing without internal supports between them.

3. A gas turbine engine according to claim 1, wherein the at least one hydro bearing is any of a hydrostatic bearing, a hydrodynamic bearing, or a hybrid hydro bearing.

4. A gas turbine engine according to claim 1, wherein the combustion chamber comprises a porous structure.

5. A gas turbine engine according to claim 1, wherein flow of the fuel directed through the at least one hydro bearing is further adapted to provide cooling to the rotor.

6. A gas turbine engine according to claim 5, wherein the flow of the fuel through the at least one hydro bearing is adapted to increase the temperature of the fuel prior to its passage to the combustion chamber.

7. A gas turbine engine according to claim 5, wherein the flow of the fuel through the at least one hydro bearing is adapted to atomize the fuel prior to combustion.

8. A gas turbine engine according to claim 1, wherein the combustion chamber is formed within the single piece housing.

9. A gas turbine engine according to claim 1, wherein the combustion chamber is disposed external to the single piece housing.

10. A gas turbine engine comprising:

a single piece rotor comprising a turbine and compressor;

a single piece housing that encloses the single piece rotor, the single piece rotor being configured to rotate within the single piece housing on at least one hydro bearing, profiles of an outer surface of the single piece rotor and an inner facing surface of the single piece housing generating surfaces of the at least one hydro bearing;

a combustion chamber adapted for the combustion of a fuel/air mixture; and at least one channel adapted to direct combustion products from the combustion chamber to the turbine, wherein at least a turbine region of the single piece rotor is formed of a material capable of withstanding higher temperatures than a material of which the single piece housing is formed.

* * * * *